US011392716B2

(12) United States Patent
Felton

(10) Patent No.: US 11,392,716 B2
(45) Date of Patent: Jul. 19, 2022

(54) MOBILE DEVICE MANAGEMENT AT A HEALTHCARE FACILITY

(71) Applicant: JAMF Software, LLC, Minneapolis, MN (US)

(72) Inventor: James Emerson Felton, Eau Claire, WI (US)

(73) Assignee: JAMF SOFTWARE, LLC, Minneapolis, MN (US)

( * ) Notice: Subject to any disclaimer, the term of this patent is extended or adjusted under 35 U.S.C. 154(b) by 0 days.

(21) Appl. No.: 15/594,226

(22) Filed: May 12, 2017

(65) Prior Publication Data

US 2018/0330115 A1     Nov. 15, 2018

(51) Int. Cl.

| | |
|---|---|
| *G06F 21/62* | (2013.01) |
| *G16H 40/20* | (2018.01) |
| *G06Q 10/10* | (2012.01) |
| *G06Q 10/00* | (2012.01) |
| *G16H 40/67* | (2018.01) |
| *G16H 10/60* | (2018.01) |

(52) U.S. Cl.
CPC ......... *G06F 21/6245* (2013.01); *G06Q 10/10* (2013.01); *G06Q 10/30* (2013.01); *G16H 10/60* (2018.01); *G16H 40/20* (2018.01); *G16H 40/67* (2018.01); *G06F 2221/2111* (2013.01)

(58) Field of Classification Search
CPC .. G06F 19/322; G06F 19/328; G06F 19/3418; G06F 8/65; G06F 21/6245; G06F 11/3419; G06F 11/3438; G06F 21/50; G06F 21/57; G06F 21/88

USPC .......................................................... 705/2
See application file for complete search history.

(56) References Cited

U.S. PATENT DOCUMENTS

| | | | |
|---|---|---|---|
| 5,164,988 | A | 11/1992 | Matyas et al. |
| 5,406,261 | A | 4/1995 | Glenn |
| 5,473,692 | A | 12/1995 | Davis |
| 5,790,664 | A | 8/1998 | Coley et al. |
| 5,825,877 | A | 10/1998 | Dan et al. |
| 6,032,257 | A | 2/2000 | Olarig et al. |
| 6,067,582 | A | 5/2000 | Smith et al. |
| 6,249,868 | B1 | 6/2001 | Sherman et al. |
| 6,385,731 | B2 | 5/2002 | Ananda |

(Continued)

FOREIGN PATENT DOCUMENTS

| | | |
|---|---|---|
| EP | 3002695 A1 | 4/2016 |
| GB | 2303726 A | 2/1997 |

(Continued)

OTHER PUBLICATIONS

Alexandrou, Alex; A security risk perception model for the adoption of mobile devices in the healthcare industry; Pace University. ProQuest Dissertations Publishing, 2016. 10097933. (Year: 2016).*

(Continued)

*Primary Examiner* — Hiep V Nguyen
(74) *Attorney, Agent, or Firm* — Benesch, Friedlander, Coplan & Aronoff LLP

(57) ABSTRACT

A method includes receiving, at a mobile device management (MDM) server, a message indicating a location at a healthcare facility. The method also includes identifying, at the MDM server, a mobile device assigned to the location. The method further includes sending a remote reset command from the MDM server to the mobile device.

20 Claims, 7 Drawing Sheets

(56) References Cited

U.S. PATENT DOCUMENTS

| | | | |
|---|---|---|---|
| 6,594,765 B2 | 7/2003 | Sherman et al. | |
| 8,447,626 B2 | 5/2013 | Sun et al. | |
| 8,627,438 B1* | 1/2014 | Bhimanaik | H04L 63/10 |
| | | | 726/9 |
| 2004/0098584 A1 | 5/2004 | Sherman et al. | |
| 2006/0237014 A1* | 10/2006 | Makinson | A61M 16/00 |
| | | | 128/204.23 |
| 2009/0112072 A1* | 4/2009 | Banet | A61B 5/7445 |
| | | | 600/301 |
| 2010/0279652 A1* | 11/2010 | Sharp | G06F 9/4843 |
| | | | 455/410 |
| 2010/0286997 A1 | 11/2010 | Srinivasan | |
| 2011/0001605 A1* | 1/2011 | Kiani | G06F 19/327 |
| | | | 340/5.6 |
| 2012/0232929 A1* | 9/2012 | Experton | G16H 10/65 |
| | | | 705/3 |
| 2012/0244886 A1* | 9/2012 | Blom | G06F 19/3493 |
| | | | 455/456.3 |
| 2013/0247166 A1* | 9/2013 | Freedman | H04L 63/02 |
| | | | 726/10 |
| 2014/0095207 A1 | 4/2014 | Dhir et al. | |
| 2014/0222450 A1 | 8/2014 | Gray | |
| 2014/0316819 A1 | 10/2014 | Dunsirn | |
| 2015/0012287 A1 | 1/2015 | Vucovich et al. | |
| 2015/0288522 A1* | 10/2015 | McCoy | H04L 9/3234 |
| | | | 726/9 |
| 2016/0026837 A1* | 1/2016 | Good | H04W 4/02 |
| | | | 340/539.13 |
| 2016/0367335 A1 | 12/2016 | Beaudry | |
| 2016/0374776 A1 | 12/2016 | Spencer et al. | |

FOREIGN PATENT DOCUMENTS

| | | |
|---|---|---|
| JP | 200421699 A | 1/2004 |
| JP | 2005275607 A | 10/2005 |
| WO | 9535533 A1 | 12/1995 |
| WO | 9703397 A1 | 1/1997 |
| WO | WO-2008096286 A1 * 8/2008 | ............... G09B 5/06 |
| WO | WO-2016164236 A1 * 10/2016 | ............. G06Q 10/08 |

OTHER PUBLICATIONS

"Outgoing Patient Administration—Registration and ADT Interface Technical Specification," Jun. 22, 2015, Epic Systems Corporation, Verona, Wisconsin, 83 pages.

"Introduction to HL7 Standards," retrieved on May 10, 2017, retrieved from <<http://www.hl7.org/implement/standards/index.cfm?ref=nav>>, Health Level Seven International, Ann Arbor, Michigan, pp. 1-2.

"HL7 Message Structure," retrieved from <<https://msdn.microsoft.com/en-us/library/ee409289(d=printer).aspx>>, retrieved on May 10, 2017, Microsoft, Redmond, Washington, pp. 1-3.

"Mobile Device Management (MDM) Protocol," retrieved from <<https://developer.apple.com/library/content/documentation/Miscellaneous/Reference . . . >>, retrieved on May 10, 2017, Apple, Inc., Cupertino, California, pp. 1-97.

Written Opinion for International Application No. PCT/US18/24794, ISA/US, dated Apr. 26, 2018, 7 pages.

Extended European Search Report dated Jan. 12, 2021 for European Application No. 18798684.9, 9 pages.

Office Action dated Mar. 1, 2022 for Japanese Application No. 2019-553026, 6 pages.

Sherman, et al., USPTO Application Data for "Method and System For Embedded, Automated Component—Level Control of Computer Systems," U.S. Appl. No. 09/047,975, filed Mar. 25, 1998, 1 page.

* cited by examiner

```
                                                            ┌─ Assigned
                                                            │  Location
                                                            │  ID 308
                                    ┌─ Transfer Message 312 │
                                    │                       │
MSH|^~\&|E|EADT|ABCD|ENG|ADT|ABCD|20160223152248|JXA9|ADT^A02|7539|P|2.5.1|||||||
EVN|A02|20160223152248||ADT_EVENT|JXA9|ADT^A02|7539|P|2.5.1|||||
PID|1|30001055^^^PID^PID^PID||TOM^ADT|||19800101|M|TOM^SNOWMAN^^~SNOWMAN^^~||123 NO
WAY^^SAN DIEGO^CA^92103^US^^^SAN DIEGO|SAN
DIEGO|(222)123-4567^^^222^1234567~^NET^Internet^t@abcd.edu~(222)321-4321^^^222^3215432|(858)987-
6543^^8^^^858^9876543|ENG|S|NON|660000011111|999-99-9999|||^^^CA^^|||C|||N|
ZPD|||NOT USED|||N||||
PD1|||ABCD MEDICAL CENTER - HILLCREST^^700|12536^CLAY^BRIAN^JONES^|||||N||||
PV1||1|OBSERVATION ADMISSION|SC^3A-ICU^PTU05^PTU05^UCLJ^^^^^|Elective||
HC10- CCU^CCU02^CCU02^UCHC^^^^^06665^MORRIS^JAMES^DREW^06665^MORRIS^JAMES^DREW^||M
PC||||RA|||06665^MORRIS^JAMES^DREW^||50000123123|WMC|||||||||Admission;Confirmed|
^^^UCLJ^^^^^^||20150831115400|||||||||||
PV2||ICU|||||20150721|||O|||||1|N|||||||||N||||
ZPV||||^^^^^^78260|||||20150831115400||||||
OBX|1|NM|HT^HEIGHT||5' 5"|ft||||||20150721|||||
OBX|2|NM|WT^WEIGHT||5291.04|oz||||||20150721|||||
```

Msg. Type 202  
Patient ID 206  
Prior Location ID 304

FIG. 3

Discharge Message 412

```
MSH|^~\&|EADT|ABCD|ENGADT|ABCD|20160309161917|JXA9|ADT^A03|7797|T|2.5|||||
EVN|A03|20160309161917||ADT_EVENT|JXA9^TOM^SMITH^^^^UC SA^^^^ABCD|20160309161900
PID|1|630010055^^^PID^PID||REGISTRATION^CASE||19800101|M|^^^^US|||||6600001302|999-99-
9999||||||||N
ZPD|||||N|N||||
PD1|||HILLCREST HOSPITAL HOD/OP^^240||||||N||||
PV1|1||INPATIENT ADMISSION|
||HC2-SICU^CU10^CU10A^UCHC^10^^^^^|Emergency||50127^MEYER^BROWN^COHEN^||INST||EO|||50127^MEYER^
BROWN^COHEN^||50000001606|SELF|||||AHR|HOME|||Discharged;Confirmed|^^^UCHC^^^^^||201
60309160055|20160309161900|7974|||||
PV2|||ICU|||||||||N||||||||||||||||||||
ZPV|||||20160309161500|20160309160055|||||||||
DG1|1||10|63.9^Cerebral infarction, unspecified^10|Cerebral infarction, unspecified|
GT1|1|4400033897|REGISTRATION^CASE^^|^^^^US|||19800101|M|P/F|Self|999-99-
9999|||||||||||
```

Msg. Type 202
Patient ID 206
Location ID 204

*FIG. 4*

MOBILE DEVICE MANAGEMENT AT A HEALTHCARE FACILITY

I. FIELD

The present disclosure is generally related to mobile device management at a healthcare facility.

II. BACKGROUND

Healthcare facilities are increasingly finding ways to improve patient experience. For example, a hospital may provide patient information, such as test results, via a website that a patient can access via a personal mobile device. A patient without a personal mobile device may be unable to access the patient information via the website. Maintaining confidentiality of sensitive patient information is a priority for healthcare facilities. Having hospital administrators (e.g., information technology (IT) professionals) delete sensitive information from each mobile device provided to a patient before giving the same mobile device to another patient is expensive in terms of time and human resources, and also likely susceptible to human error. Even a small risk of a hospital administrator failing to delete sensitive patient information from a mobile device before providing the mobile device to another patient may be prohibitive in a healthcare setting.

III. SUMMARY

Systems and methods of managing mobile devices in a healthcare facility are disclosed. Mobile devices are available at a healthcare facility for patient use. The mobile devices are assigned to various locations at the healthcare facility (e.g., a hospital, a clinic, or both). For example, a mobile device may be assigned to a hospital bed, a hospital room, or both. To illustrate, the mobile device may be attached to the hospital bed or a wall of the hospital room with a cable. A healthcare system maintains a mapping between a location and an assigned mobile device. For example, location-to-device mapping data indicates a mapping between a location identifier (ID) of the location and a device ID of the assigned mobile device. A user (e.g., a hospital administrator) may assign the hospital bed to a patient when the patient is admitted to the hospital or when the patient is transferred from another location in the hospital. For example, the healthcare system includes a healthcare management system. The user provides user input to the healthcare management system indicating that the location (e.g., the hospital bed) is assigned to the patient on admittance, or that the patient is transferred to the location from another location of the healthcare facility. Alternatively, the user may provide input to the healthcare system indicating that the patient is no longer assigned to the location. For example, the user provides user input to the healthcare management system indicating that the patient is transferred from the location to another location of the healthcare facility or that the patient is discharged from the healthcare facility. The healthcare management system is configured to generate, based on the user input, a first message indicating that the patient is assigned to a location upon admittance, a message indicating that the patient is transferred from one location to another location of the healthcare facility, or a message indicating that the patient is discharged from the healthcare facility.

The healthcare system includes a healthcare listener coupled to the healthcare management system and to a mobile device management (MDM) server. The healthcare listener is configured to receive messages from the healthcare management system. The MDM server is configured to determine whether a patient is admitted, transferred, or discharged based on the messages received by the healthcare listener. For example, the MDM server may query the healthcare listener to determine which messages have been received by the healthcare listener. The healthcare listener sends a second message to the MDM server indicating that the healthcare listener received a first message from the healthcare management system. In a particular implementation, the healthcare listener sends the second message to the MDM server in response to receiving an update request from the MDM server. For example, the MDM server sends the update request to the healthcare listener at particular time intervals (e.g., periodically). Alternatively, or in addition, the healthcare listener may send the second message to the MDM server independently of receiving an update request from the MDM server. For example, the healthcare listener sends a message update (e.g., the second message) to the MDM server in response to receiving each message (e.g., the first message) from the healthcare management system. As another example, the healthcare listener sends a message update (e.g., the second message) to the MDM server at particular time intervals. The second message may correspond to one or more messages received by the healthcare listener from the healthcare management system during a particular time window. The second message indicates that the patient is assigned to a location upon admittance, that the patient is transferred from one location to another location of the healthcare facility, or that the patient is discharged from the healthcare facility.

The MDM server is configured to manage mobile devices of the healthcare facility. The MDM server determines that a patient is assigned to a location (e.g., the hospital bed) in response to determining that the second message indicates that the patient has been assigned to the location upon admittance to the healthcare facility or that the patient has been transferred to the location. The MDM server, in response to determining that the patient is assigned to the location, identifies a mobile device assigned to the location based on the location-to-device mapping data. The MDM server may initiate provisioning of data (and applications) associated with the patient to the identified mobile device. The data includes patient records, medical information, application data, or a combination thereof. For example, the patient records may indicate names of hospital staff assigned to treat the patient. The application data may correspond to an entertainment application (e.g., a gaming application) that is targeted to a user characteristic (e.g., age, gender, education, profession, etc.) associated with the patient. The application data includes the application (e.g., an executable file), an identifier of the application, a universal resource locator (URL) associated with the application, or a combination thereof. The medical information may be related to a symptom or a diagnosis associated with the patient.

The MDM server determines that a patient is no longer assigned to the location (e.g., the hospital bed) in response to determining that the second message indicates that the patient has been discharged from the healthcare facility or that the patient has been transferred from the location to another location (e.g., another hospital bed) at the healthcare facility. The MDM server is configured to, in response to determining that the patient is no longer assigned to the location, send a reset command to the mobile device. The reset command indicates that personally identifiable information associated with the patient, protected health information associated with the patient, or both, is to be deleted from the mobile device. For example, the reset command may correspond to a factory reset command and may indicate that all user data is to be deleted from the mobile device. The mobile device may delete the user data (e.g., including information associated with the patient) in response to receiving the reset command.

A push notification service is coupled to the MDM server and the mobile device. The push notification service corresponds to a trusted source for the mobile device. For example, the push notification service may be associated with (e.g., provided by) a manufacturer of the mobile device. The MDM server is configured to send a notification request to the push notification service in response determining that the mobile device is assigned to the location. The push notification service is configured to send a push notification to the mobile device in response to receiving the notification request from the MDM server. The push notification may indicate that the mobile device is to check-in with the MDM server. The mobile device may send a message (e.g., a check-in message) to the MDM server in response to receiving the push notification. The MDM server may send the data associated with the patient to the mobile device based on determining that the patient is assigned to the location and based on receiving the message from the mobile device. In a particular example, the MDM server sends the reset command to the mobile device prior to sending the data to the mobile device. To illustrate, the MDM server may send the reset command to the mobile device to "clear" the mobile device prior to sending the data to the mobile device. The MDM server may send the reset command to the mobile device based on determining that the patient is no longer assigned to the location and based on receiving the message from the mobile device.

In a particular aspect, a method includes receiving, at a mobile device management (MDM) server, a message indicating a location at a healthcare facility. The method also includes identifying, at the MDM server, a mobile device assigned to the location. The method further includes sending a remote reset command from the MDM server to the mobile device. For example, the MDM server sends a notification request to a push notification service in response to determining that the message indicates that the patient has been transferred from the location or discharged from the healthcare facility. The push notification service sends a push notification to the mobile device in response to receiving the notification request from the MDM server. The mobile device sends a message to the MDM server in response to receiving the push notification from the push notification service. The MDM server sends the remote reset command to the mobile device in response to receiving the message from the mobile device.

In another particular aspect, a computer-readable storage device stores instructions that, when executed by a processor, cause the processor to perform operations including receiving a message including a patient identifier, the message indicating a location at a healthcare facility. The operations also include identifying a mobile device assigned to the location. The operations further include initiating provision of data associated with the patient identifier to the mobile device. For example, the data may be provided to the mobile device based at least in part on determining that the message indicates that the patient has been assigned to the location upon admittance to the healthcare facility or that the patient has been transferred to the location from another location of the healthcare facility.

In another particular aspect, a computer system includes a healthcare listener device and a mobile device management (MDM) server. The healthcare listener device is configured to receive a first message indicating a location at a healthcare facility. The healthcare listener device is also configured to send a second message to the MDM server indicating the location. The MDM server is configured, in response to receiving the second message from the healthcare listener device, to identify a mobile device assigned to the location, and to send a remote reset command to the mobile device.

Other aspects, advantages, and features of the present disclosure will become apparent after review of the entire application, including the following sections: Brief Description of the Drawings, Detailed Description, and the Claims.

IV. BRIEF DESCRIPTION OF THE DRAWINGS

FIG. 3 is a diagram of a particular illustrative aspect of a transfer message generated by the system of FIG. 1;

FIG. 4 is a diagram of a particular illustrative aspect of a discharge message generated by the system of FIG. 1;

V. DETAILED DESCRIPTION

Figure 1:
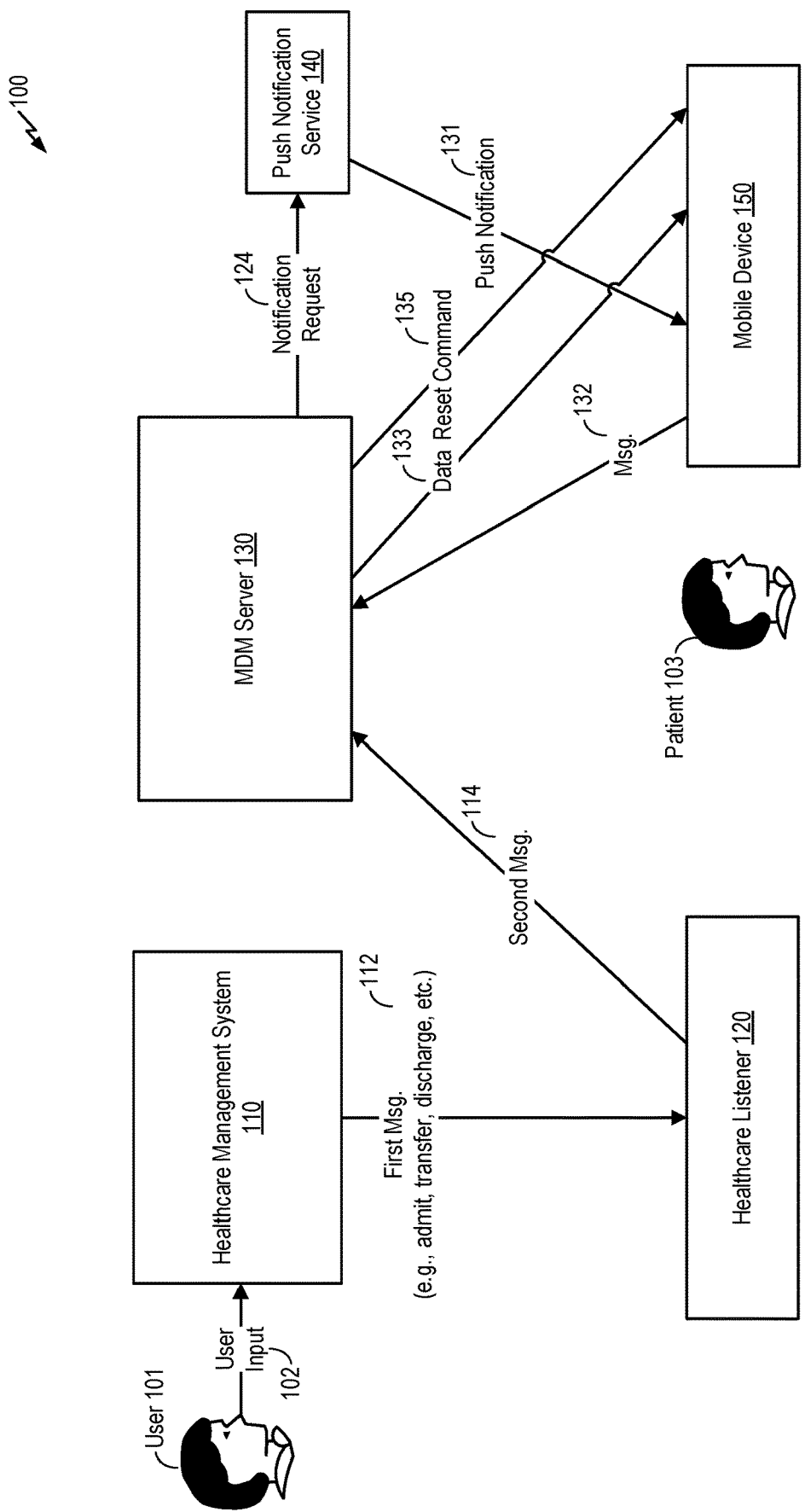
FIG. 1 is a block diagram of a particular illustrative aspect of a system operable to perform mobile device management at a healthcare facility.

Referring to FIG. 1, a system is shown and generally designated 100. The system 100 (e.g., a computer system) includes a healthcare management system 110 coupled, via a healthcare listener 120, to a MDM server 130. The MDM server 130 is coupled to a push notification service 140 and to a mobile device 150. The healthcare management system 110 is configured to generate admit-discharge-transfer (ADT) messages indicating a patient status. For example, the healthcare management system 110 generates a message when a patient is admitted to a healthcare facility, a message when the patient is transferred from one location to another location at the healthcare facility, a message when the patient is discharged from the healthcare facility, or a combination thereof.

The healthcare listener 120 is configured to track the ADT messages. For example, the healthcare listener 120 receives the messages from the healthcare management system 110. The healthcare listener 120 may store data in a memory indicating that the messages have been received. The MDM server 130 may be configured to query the healthcare listener 120 to determine whether any ADT messages have been received from the healthcare management system 110. The MDM server 130 is configured to, in response to determining that an ADT message has been received from the healthcare management system 110, send a reset command 135 to the mobile device 150 or initiate provisioning of data 133 to the mobile device 150.

During operation, a user 101 (e.g., a healthcare administrator) admits a patient 103 (e.g., "Tom Snowman") to a healthcare facility. The user 101 provides user input 102 to the healthcare management system 110 indicating that the patient 103 has been admitted and that the patient 103 has been assigned to a particular location at the healthcare facility. The particular location includes a bed, a room, a floor, a building, a unit, a facility, a section, or a combination thereof. For example, the particular location may correspond to a particular bed (e.g., Bed number 2) in a particular unit (e.g., Coronary Care Unit) of a particular building (e.g., Building A) of the healthcare facility. As another example, the particular location may correspond to a particular room (e.g., Room 2) of a particular section (e.g., Emergency Room) of the healthcare facility. The healthcare management system 110 generates a first message 112 indicating that the patient 103 is assigned to the particular location.

The first message 112 may correspond to an ADT message. A value (e.g., "ADT_A01") of a first field of the first message 112 may indicate that the first message 112 corresponds to an admit message. The first field of the first message 112 may include a message header field, a message type field, an event type field, an event type code field, or a combination thereof. A value (e.g., "30001055") of a second field of the first message 112 identifies the patient 103. The second field may include a patient identification field, a patient ID list field, a patient name field, a patient alias field, a social security number (SSN) field, a driver's license number field, or a combination thereof. A value (e.g., "CCU02") of a third field of the first message 112 may indicate the particular location (e.g., Bed number 2 of a Coronary Care Unit). The third field may include a bed status update field, a patient visit field, an assigned patient location field, or a combination thereof.

The healthcare listener 120 receives the first message 112. The healthcare listener 120 sends a second message 114 to the MDM server 130. The healthcare listener 120 sends the second message 114 to the MDM server 130 in response to receiving the first message 112 from the healthcare management system 110. In a particular aspect, the healthcare listener 120 sends the second message 114 to the MDM server 130 in response to receiving an update request from the MDM server 130. For example, the healthcare listener 120 may maintain a record of messages received from the healthcare management system 110. The healthcare listener 120, in response to receiving the first message 112 at a first time, adds an entry in memory indicating that the first message 112 has been received from the healthcare management system 110 at the first time. The MDM server 130 may send the update request to the healthcare listener 120 at particular time intervals. The particular time intervals may be based on a configuration setting, a default value, user input, or a combination thereof. The healthcare listener 120, in response to receiving an update request from the MDM server 130, generates the second message 114 based on the entry and sends the second message 114 to the MDM server 130.

In a particular aspect, the healthcare listener 120 sends the second message 114 to the MDM server 130 independently of receiving an update request from the MDM server 130. For example, the healthcare listener 120 sends a message update (e.g., the second message 114) to the MDM server 130 in response to receiving each message (e.g., the first message 112) from the healthcare management system 110 and determining that the message has a particular message type (e.g., admit, transfer, or discharge). In this example, the second message 114 corresponds to a single message (e.g., the first message 112) received from the healthcare management system 110. As another example, the healthcare listener 120 sends a message update (e.g., the second message 114) to the MDM server 130 at particular time intervals (e.g., periodically). In this example, the second message 114 corresponds to one or more messages received by the healthcare listener 120 from the healthcare management system 110 during a particular time window.

The second message 114 indicates that the patient 103 is assigned to the particular location. For example, the second message 114 indicates that the patient 103 is assigned to the particular location upon admittance to the healthcare facility or that the patient 103 is transferred to the particular location from another location at the healthcare facility. In a particular aspect, each of the first message 112 and the second message 114 includes a patient ID of the patient 103, a location ID of the particular location, a message type (e.g., admit, transfer, or discharge) of the first message 112, or a combination thereof, as further described with reference to FIG. 2. For example, each of the first message 112 and the second message 114 includes the message type (e.g., discharge) of the first message 112 and the patient ID of the patient 103. In a particular implementation, each of the first message 112 and the second message 114 includes the location ID of the particular location (e.g., a hospital bed) indicating that the patient 103 is discharged from the particular location of the healthcare facility. In an alternative implementation, the location ID is absent from the first message 112, the second message 114, or both. In this implementation, each of the first message 112 and the second message 114 indicates that the patient 103 is discharged from the healthcare facility. Each of the first message 112 and the second message 114 may implicitly indicate that the patient 103 is discharged from a previously assigned location (e.g., the particular location) without explicitly including the location ID.

The MDM server 130 determines that the mobile device 150 is assigned to the particular location, as further described with reference to FIG. 2. For example, the MDM server 130 may determine that location-to-device mapping data indicates that the location ID of the particular location corresponds to (e.g., is assigned to) a device ID of the mobile device 150.

The MDM server 130 may send a notification request 124 to the push notification service 140 to initiate transmission of a push notification 131 to the mobile device 150. The push notification service 140 sends the push notification 131 to the mobile device 150 in response to receiving the notification request 124 and determining that the notification request 124 indicates the mobile device 150. The push notification 131 instructs the mobile device 150 to check-in with the MDM server 130. For example, the push notification service 140 may be a trusted source for the mobile device 150 and the push notification 131 may indicate that the MDM server 130 is a trusted device. The MDM server 130 may receive a message 132 from the mobile device 150 responsive to the push notification 131. For example, the mobile device 150 sends the message 132 to the MDM server 130 in response to receiving the push notification 131. The MDM server 130 may, in response to receiving the message 132, send data 133 to the mobile device 150, as further described with reference to FIG. 2. The data 133 is associated with the patient 103, as further described with reference to FIG. 2. For example, the data 133 includes at least one of a patient record, medical information, application data, or a configuration setting that is associated with the patient 103.

In a particular aspect, the MDM server 130 sends the reset command 135 to the mobile device 150 prior to sending the data 133 to the mobile device 150. The reset command 135 may correspond to a factory reset command. To improve patient confidentiality (e.g., patient privacy), the mobile device 150 may delete user data stored at the mobile device 150 in response to receiving the reset command 135. The user data may correspond to a user (e.g., a patient) that previously used the mobile device 150. The mobile device 150 may receive the data 133 from the MDM server 130 subsequent to deleting the user data stored at the mobile device 150.

In a particular aspect, the healthcare management system 110 generates the first message 112 in response to determining that the patient 103 is transferred from a first location to a second location. A value (e.g., "ADT_A02") of a first field of the first message 112 may indicate that the first message 112 corresponds to a transfer message. A value (e.g., "30001055") of a second field of the first message 112 may identify the patient 103. A value (e.g., "CCU02") of a third field of the first message 112 may indicate the first location (e.g., Bed number 2 of a Coronary Care Unit). The third field may include a bed status update field, a patient visit field, a prior location field, or a combination thereof. A value (e.g., "PTU05") of a fourth field of the first message 112 may indicate the second location (e.g., Room number 5 of a Patient Treatment Unit). The fourth field may include a bed status update field, a patient visit field, an assigned patient location field, or a combination thereof.

The MDM server 130 may send the reset command 135 to the mobile device 150 in response to receiving the message 132 indicating that the patient 103 is transferred from the first location, determining that the mobile device 150 is assigned to the first location, determining that the mobile device 150 is assigned to the patient 103, or a combination thereof. The reset command 135 may indicate that personally identifiable information associated with the patient 103, protected health information associated with the patient 103, or both, are to be deleted from the mobile device 150. The mobile device 150 may, in response to receiving the reset command 135, delete the data 133 stored at the mobile device 150. Alternatively, the MDM server 130 may, in response to receiving the message 132 indicating that the patient 103 is transferred to the second location and that the mobile device 150 is assigned to the second location, send the data 133 to the mobile device 150. In a particular aspect, the MDM server 130 sends the reset command 135 to the mobile device 150 prior to sending the reset command 135 to the mobile device 150. The mobile device 150 may, in response to receiving the reset command 135, delete user data corresponding to a previous user of the mobile device 150.

In a particular aspect, the healthcare management system 110 generates the first message 112 in response to determining that the patient 103 is discharged from a particular location (e.g., the hospital bed or the hospital room) or from the healthcare facility. A value (e.g., "ADT_A03") of a first field of the first message 112 indicates that the first message 112 corresponds to a discharge message. A value (e.g., "30001055") of a second field of the first message 112 identifies the patient 103. A value (e.g., "ICU10") of a third field of the first message 112 may indicate the particular location (e.g., Bed 10 of an Intensive Care Unit). The third field may include a bed status update field, a patient visit field, a prior location field, or a combination thereof.

The MDM server 130 may send the reset command 135 to the mobile device 150 in response to receiving the message 132 indicating that the patient 103 is discharged from the particular location and that the mobile device 150 is assigned to the particular location. Alternatively, the MDM server 130 may send the reset command 135 to the mobile device 150 in response to receiving the message 132 indicating that the mobile device 150 was assigned to the patient 103 and that the patient 103 is discharged.

The system 100 may thus enable the patient 103 to access sensitive information or targeted information using the mobile device 150 provided by the healthcare facility. To improve patient privacy, the information (e.g., the data 133) may be deleted from the mobile device 150 once the particular location (e.g., the hospital bed or the hospital room) is no longer assigned to the patient 103. For example, the MDM server 130 may send the reset command 135 instructing the mobile device 150 to delete patient data (e.g., the data 133) in response to a determination that the patient will no longer be associated with the mobile device 150.

Figure 2:
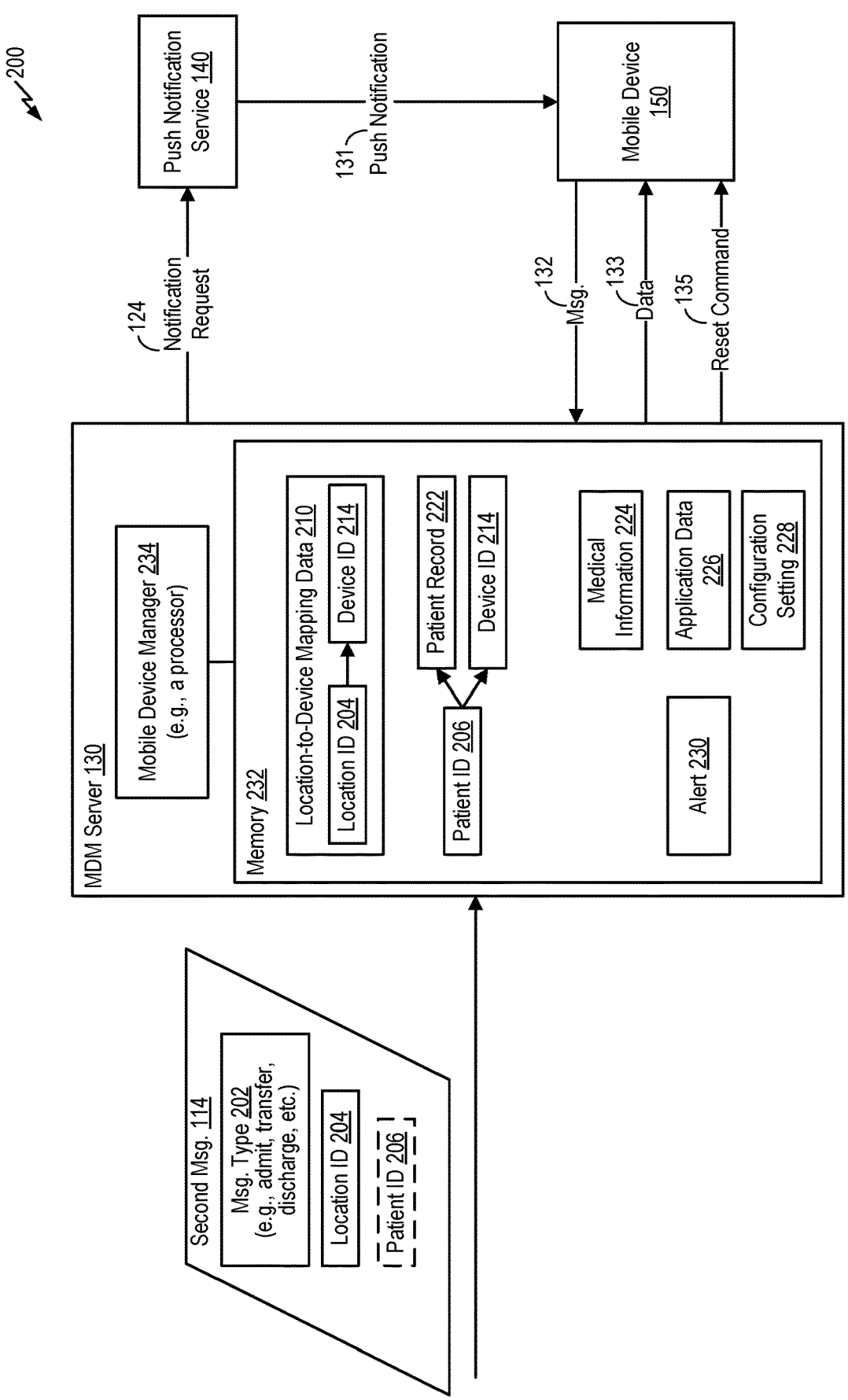
FIG. 2 is a diagram of a particular illustrative aspect of the system of FIG. 1.

Referring to FIG. 2, a system is disclosed and generally designated 200. The system 200 may correspond to the system 100. For example, the system 200 includes the MDM server 130 coupled to the push notification service 140 and to the mobile device 150. The MDM server 130 includes a mobile device manager 234 (e.g., a processor) coupled to a memory 232.

In a particular aspect, the mobile device manager 234 corresponds to a processor configured to perform one or more operations described herein. In a particular aspect, the mobile device manager 234 corresponds to instructions that, when executed by a processor, cause the processor to perform one or more operations described herein. In a particular aspect, the mobile device manager 234 corresponds to a computer-readable storage device that stores instructions that are executable to perform one or more operations described herein.

The mobile device manager 234 may be configured to send the reset command 135, the data 133, or both, to the mobile device 150, as described herein. The memory 232 may be configured to store location-to-device mapping data 210. The location-to-device mapping data 210 may indicate that one or more mobile devices are assigned to one or more locations at the healthcare facility. For example, the location-to-device mapping data 210 indicates that a device ID 214 of the mobile device 150 is assigned to a location ID 204 of a particular location of the healthcare facility. The device ID 214 may include a media access control (MAC) address of the mobile device 150, an internet protocol (IP) address of the mobile device 150, or another device ID.

In a particular aspect, the MDM server 130 receives the location-to-device mapping data 210 from another device. In an alternative aspect, the MDM server 130 generates the location-to-device mapping data 210. For example, the user 101 of FIG. 1 (or another user) may assign the mobile device 150 to the particular location (e.g., a hospital bed or a hospital room). The MDM server 130 may, in response to receiving a user input indicating that the mobile device 150 is assigned to the particular location, generate (or update) the location-to-device mapping data 210 indicating that the mobile device 150 is assigned to the particular location.

The memory 232 is configured to store patient data. For example, the memory 232 stores a patient record 222 of the patient 103. The memory 232 may indicate that the patient record 222 is assigned to the patient 103 having a patient ID 206. The memory 232 may be configured to store medical information 224. The medical information 224 may be associated with a particular symptom (e.g., high cholesterol), a particular diagnosis (e.g., heart disease), or both. The memory 232 may be configured to store application data 226. The application data 226 corresponds to an application, such as an entertainment application, an educational application, a healthcare application, or a combination thereof.

The application data 226 includes the application (e.g., an executable file), an identifier of the application, a universal resource locator (URL) associated with the application, or a combination thereof. The memory 232 may include a configuration setting 228. The configuration setting 228 may include a username, a password, or both.

During operation, as described with reference to FIG. 1, the MDM server 130 receives the second message 114 from the healthcare listener 120. The second message 114 indicates a message type 202 (e.g., admit, transfer, or discharge), a location ID 204, a patient ID 206 of the patient 103, or a combination thereof. For example, the second message 114 is based on the first message 112. The healthcare listener 120 may determine the message type 202 based on a value of a first field of the first message 112. For example, a first value (e.g., "ADT_01"), a second value (e.g., "ADT_02"), and a third value (e.g., "ADT_03") of the first field corresponds to a first message type (e.g., an admit message type), a second message type (e.g., a transfer message type), and a third message type (e.g., a discharge message type), respectively. The healthcare listener 120 may determine the patient ID 206 based on a value (e.g., "30001055") of a second field of the first message 112.

The healthcare listener 120 may determine the location ID 204 based on a value of a third field of the first message 112 or a value of a fourth field of the first message 112. For example, the healthcare listener 120, in response to determining that the first message 112 corresponds to an admit message, determines the location ID 204 based on an assigned patient location field of the first message 112. The healthcare listener 120, in response to determining that the first message 112 corresponds to a discharge message, determines the location ID 204 based on a prior location field of the first message 112.

The healthcare listener 120, in response to determining that the first message 112 corresponds to a transfer message, determines a first location ID based on a prior location field of the first message 112, a second location ID based on an assigned patient location field of the first message 112, or both. The first message 112 may indicate that the patient 103 is transferred from a first location corresponding to the first location ID to a second location corresponding to the second location ID. The healthcare listener 120 generates the second message 114 to indicate the first location ID, the second location ID, or both. The location ID 204 may correspond to the first location ID or the second location ID.

The mobile device manager 234 may determine whether the patient 103 is assigned to a particular location based on the second message 114. For example, the mobile device manager 234 determines that the patient 103 is assigned to the particular location in response to a determination that the message type 202 indicates an admit message and that the second message 114 indicates that the patient 103 (corresponding to the patient ID 206) is assigned to the particular location based on the location ID 204. The mobile device manager 234, in response to determining that the patient 103 is assigned to the particular location, identifies one or more mobile devices assigned to the particular location. For example, the mobile device manager 234 determines that the mobile device 150 is assigned to the particular location in response to determining that the location-to-device mapping data 210 indicates that the location ID 204 corresponds to the device ID 214.

The mobile device manager 234 may, in response to determining that the location ID 204 corresponds to the device ID 214, store data in the memory 232 indicating that the patient ID 206 corresponds to the device ID 214. For example, the mobile device manager 234 stores data in the memory 232 indicating that the mobile device 150 is assigned to the patient 103 of FIG. 1.

The mobile device manager 234 may send the notification request 124 to the push notification service 140 in response to determining that the location ID 204 corresponds to the device ID 214. The notification request 124 includes the device ID 214. The push notification service 140 sends the push notification 131 to the mobile device 150 in response to receiving the notification request 124 from the MDM server 130 and determining that the notification request 124 indicates the device ID 214. The push notification 131 may identify the MDM server 130. For example, the push notification 131 indicates an address (e.g., a MAC address, an IP address, or both) of the MDM server 130. The mobile device 150 sends the message 132 to the MDM server 130 in response to receiving the push notification 131 and determining that the push notification 131 identifies the MDM server 130. The push notification service 140 may be a trusted source for the mobile device 150. The mobile device 150 may communicate with the MDM server 130 in response to determining that the push notification 131 from the push notification service 140 identifies the MDM server 130.

The mobile device manager 234 generates the data 133 in response to receiving the second message 114 from the healthcare listener 120 of FIG. 1, receiving the message 132 from the mobile device 150, or both. The data 133 may include the patient record 222, the medical information 224, the application data 226, the configuration setting 228, or a combination thereof. The mobile device manager 234 retrieves the patient record 222 based on the patient ID 206. The patient record 222 may indicate (or identify) medical personnel assigned to care for the patient 103, a medication prescribed to the patient 103, a test result of the patient 103, a message for the patient 103, a symptom (e.g., high cholesterol) indicated by the patient 103, a diagnosis (e.g., heart disease) of the patient 103, a profession (e.g., a stunt person) of the patient 103, a habit (e.g., a smoker) of the patient 103, an educational level of the patient 103, the age of the patient 103, or a combination thereof.

The mobile device manager 234 may retrieve (or identify) the medical information 224 based on the patient record 222. For example, the mobile device manager 234 retrieves the medical information 224 corresponding to the symptom, the diagnosis, the profession, the habit, the educational level, the age, or a combination thereof, indicated by the patient record 222. The medical information 224 may include educational material that is selected by a medical professional and that is targeted to the patient 103.

The mobile device manager 234 may select the application data 226 based on the patient record 222. For example, the mobile device manager 234 selects an application based on the age, the educational level, the symptom, the diagnosis, the profession, the habit, or a combination thereof, indicated by the patient record 222. The application is targeted to the patient 103. For example, the application includes computer games that are targeted to users of the same age as the patient 103. The application data 226 corresponds to the selected application. For example, the application data 226 includes the selected application, an identifier of the selected application, a download URL of the selected application, or a combination thereof. The download URL indicates a location from which the selected application is retrievable. The location may be associated with the MDM server 130 or another device.

In a particular aspect, the application data 226 includes a manifest URL of a manifest file. The manifest URL indicates a location of the manifest file, and the manifest file indicates the download URL of the selected application. The mobile device manager 234 generates (or selects) the manifest file based on the patient record 222. For example, the mobile device manager 234 selects the application based on the patient record 222 and generates the manifest file to indicate the selected application. As another example, the mobile device manager 234 selects the manifest file based on the age, the educational level, the symptom, the diagnosis, the profession, the habit, or a combination thereof, indicated by the patient record 222. The manifest file indicates one or more applications targeted to the patient 103.

The mobile device manager 234 may generate the configuration setting 228 based on the patient ID 206, the patient record 222, or both. For example, the mobile device manager 234 generates the configuration setting 228 to indicate the patient ID 206, the age, the educational level, the symptom, the diagnosis, the profession, the habit, or a combination thereof.

The mobile device manager 234 may send the data 133 to the mobile device 150 in response to receiving the message 132 from the mobile device 150. In an alternative aspect, the mobile device manager 234 sends the data 133 independently of receiving the message 132 from the mobile device 150. In this aspect, the MDM server 130 may be a trusted source for the mobile device 150 and the mobile device 150 may accept the data 133 from the MDM server 130 independently of having sent the message 132 to the MDM server 130.

In a particular aspect, the data 133 includes the patient record 222. In this aspect, the mobile device 150 enables the patient 103 to access the patient record 222. For example, the patient 103 uses the mobile device 150 to identify the medical personnel assigned to care for the patient 103. As another example, the patient 103 uses the mobile device 150 to verify whether the patient record 222 includes accurate information about the patient 103. To illustrate, the patient 103 may confirm whether allergy information of the patient 103 is accurately indicated in the patient record 222. The patient 103 may inform hospital personnel in response to detecting inaccurate information in the patient record 222.

In a particular aspect, the data 133 includes the medical information 224. In this aspect, the mobile device 150 enables the patient 103 to access the medical information 224. For example, the patient 103 uses the mobile device 150 to review the medical information 224 associated with a diagnosis of the patient 103. Having access to the medical information 224 enables the patient 103 to make well-informed healthcare decisions.

In a particular aspect, the data 133 includes the application data 226. In this aspect, the mobile device 150 enables the patient 103 to access an application corresponding to the application data 226. For example, the application data 226 includes the application and the mobile device 150 stores (e.g., installs) the application at the mobile device 150. As another example, the mobile device 150 retrieves the application based on an application identifier (e.g., URL) indicated by the application data 226. The application identifier is associated with the MDM server 130 or another device. In a particular example, the application data 226 includes a manifest URL indicating a location of a manifest file. In this example, the MDM server 130 may send the application data 226 as an install application command to the mobile device 150. The install application command may indicate the manifest URL. The mobile device 150 retrieves the manifest file based on the manifest URL. The manifest file indicates the application identifier (e.g., URL). The mobile device 150 retrieves the application based on the application identifier indicated by the manifest file. In a particular aspect, the manifest file indicates multiple application identifiers associated with multiple applications. The mobile device 150 retrieves the applications based on the application identifiers. The application data 226 may correspond to one or more targeted applications. For example, the patient 103 uses the mobile device 150 to play computer games (e.g., chess) that are targeted to users of the same age as the patient 103.

In a particular aspect, the data 133 includes the configuration setting 228. In this aspect, the mobile device 150 is configured for the patient 103 based on the configuration setting 228. For example, the mobile device 150 provides a username and a password to a web-based application based on the configuration setting 228, and the patient 103 accesses the web-based application via the mobile device 150 without having to type the username and the password.

In a particular aspect, the mobile device manager 234 sends the reset command 135 to the mobile device 150 prior to sending the data 133 to the mobile device 150. The mobile device 150 may, in response to receiving the reset command 135, delete user data stored at the mobile device 150. For example, the mobile device 150 deletes a patient record, medical information, application data, an application, a configuration, or a combination thereof, associated with a previous user of the mobile device 150.

The mobile device manager 234 may thus enable the mobile device 150 to be automatically set up for use by the patient 103 in response to receiving a message (e.g., the second message 114 based on the first message 112 of FIG. 1) indicating that the patient 103 is admitted to the healthcare facility. The functionality to automatically set up mobile devices may be added to the system 100 independently of modifications to the healthcare management system 110. The healthcare management system 110 may include a legacy healthcare management system, an independently managed healthcare management system, or both.

In a particular aspect, the mobile device manager 234 generates an alert 230 (e.g., a message) in response to determining that the message 132 has not been received from the mobile device 150 within a particular duration of sending the notification request 124 to the push notification service 140. The particular duration may correspond to a configuration setting, a default value, a user input, or a combination thereof. The mobile device manager 234 may send the alert 230 to a device, a user, or both. For example, the mobile device manager 234 sends the alert 230 to an electronic mail (e-mail) account of the user 101 (or another healthcare administrator).

The user 101 (or another healthcare administrator) may check on the mobile device 150 in response to receiving the alert 230. For example, if the mobile device 150 is not powered up, the user 101 powers up the mobile device 150. The mobile device 150 may receive the push notification 131 from the push notification service 140 subsequent to powering up. As another example, if the mobile device 150 is not working properly, the user 101 assigns another mobile device to the particular location (e.g., hospital bed or hospital room) that corresponds to the location ID 204. In this example, the mobile device manager 234, in response to receiving updated location-to-device mapping data indicating that a second mobile device having a second device ID is assigned to the particular location corresponding to the location ID 204, sends an updated notification request 124 to the push notification service 140 indicating the second device ID. The push notification service 140 sends the push notification 131 to the second mobile device corresponding to second device ID. The second mobile device sends the message 132 to the MDM server 130 and receives the data 133 from the MDM server 130.

In a particular aspect, the mobile device manager 234 determines that the patient 103 is assigned to a particular location in response to determining that the message type 202 indicates a transfer message and that the second message 114 indicates that the patient 103 (e.g., "Tom Snowman") corresponding to the patient ID 206 is transferred to a particular location corresponding to the location ID 204. Operations performed by the mobile device manager 234 in response to determining that the patient 103 is transferred to the particular location may include one or more operations performed by the mobile device manager 234 in response to determining that the patient 103 is admitted to the healthcare facility and assigned to the particular location.

In a particular aspect, the mobile device manager 234 determines, based on the second message 114, that the patient 103 is no longer assigned to a particular location. For example, the mobile device manager 234 determines that the patient 103 is no longer assigned to a particular location in response to determining that the message type 202 indicates a transfer message and that the second message 114 indicates that the patient 103 is transferred from the particular location. As another example, the mobile device manager 234 determines that the patient 103 is no longer assigned to a particular location in response to determining that the message type 202 indicates a discharge message.

Operations performed by the mobile device manager 234 in response to determining that the patient 103 is discharged may include one or more operations performed by the mobile device manager 234 in response to determining that the patient 103 is transferred from the particular location. For example, the mobile device manager 234 identifies the mobile device 150 in response to determining that the patient 103 is no longer assigned to a particular location. In a particular aspect, the second message 114 indicates the location ID 204 of the particular location, and the mobile device manager 234 identifies the mobile device 150 based on the location-to-device mapping data 210. In an alternative aspect, the mobile device manager 234 identifies the mobile device 150 in response to determining that data stored in the memory 232 indicates that the mobile device 150 having the device ID 214 is assigned to the patient 103 having the patient ID 206.

The mobile device manager 234, in response to identifying the mobile device 150, sends the reset command 135 to the mobile device 150. The mobile device 150 may, in response to receiving the reset command 135, delete user information associated with the patient 103 stored at the mobile device 150. For example, the mobile device 150, in response to receiving the reset command 135, deletes the data 133 stored at the mobile device 150. As another example, the mobile device 150, in response to receiving the reset command 135, performs a factory reset of the mobile device 150. Performing the factory reset may restore the mobile device 150 to original manufacturer settings. For example, the mobile device 150 performs the factory reset by deleting all user data, including the data 133, stored at the mobile device 150. The mobile device manager 234 may update the memory 232 to remove the association between the patient ID 206 and the device ID 214.

The system 200 thus enables automatic set up of the mobile device 150 for use by the patient 103 while the patient 103 is assigned to a particular location corresponding to the mobile device 150. The system 200 also improves patient privacy by enabling automatic deletion of user data of the patient 103 stored at the mobile device 150 once the patient 103 is no longer assigned to the particular location. For example, the mobile device manager 234 sends the reset command 135 instructing the mobile device 150 to delete patient data (e.g., the data 133) in response to a determination that the patient will no longer be associated with the mobile device 150.

Referring to FIG. 3, a transfer message is shown and generally designated 312. The transfer message 312 may be generated by the healthcare management system 110, the healthcare listener 120, the system 100 of FIG. 1, or a combination thereof. The transfer message 312 may correspond to the first message 112, the second message 114 of FIG. 1, or both. The transfer message 312 may comply with an ADT message specification. In a particular aspect, the transfer message 312 complies with a health level seven (HL7) format. For example, the transfer message 312 complies with a HL7 version 1 format, a HL7 version 2 format, a HL7 version 3 format, a HL7 fast healthcare interoperability resources (FHIR) format, another HL7 format, or a combination thereof.

The transfer message 312 indicates the message type 202 (e.g., "A02"). A value (e.g., "A02") of the message type 202 indicates that the transfer message 312 corresponds to a transfer message. The transfer message 312 indicates the patient ID 206 (e.g., "30001055"). A value (e.g., "30001055") of the patient ID 206 indicates that the corresponding patient 103 is transferred. The transfer message 312 indicates a prior location ID 304 (e.g., "HC 10-CCU^CCU02^CCU02^UCHC^1^^^^^^"). A value (e.g., "HC 10-CCUACCU02^CCU02^UCHC^1^^^^^^") of the prior location ID 304 indicates that the patient 103 is transferred from a corresponding first location (e.g., Coronary Care Unit Bed 2). It should be understood that a particular field (e.g., "HC 10-CCU^CCU02^CCU02^UCHC^1^^^^^^") of the transfer message 312 is indicated as corresponding to the prior location ID 304 for ease of illustration, in some implementations one or more portions of the field, multiple fields of the transfer message 312, one or more portions of multiple fields of the transfer message 312, or a combination thereof, correspond to the prior location ID 304. In a particular example, a particular portion (e.g., "CCU02") of the field corresponds to the prior location ID 304. In an alternate example, the healthcare facility may include multiple hospital beds with the same name (e.g., "CCU02"). In this example, a particular hospital bed is uniquely identified by a portion (e.g., "CCU02") of the field combined with additional information indicating a location (e.g., a room, a building, a floor, a unit, a section, a facility, or a combination thereof) of the particular hospital bed. The additional information is indicated by one or more additional portions of the field of the transfer message 312, one or more additional fields of the transfer message 312, or a combination thereof.

The transfer message 312 indicates an assigned location ID 308 (e.g., "SC 3^-ICU^PTU05^PTU05^UCLJ^^^^^^") A value (e.g., "SC 3^-ICU^PTU05^PTU05^UCLJ^^^^^^") of the assigned location ID 308 indicates that the patient 103 is transferred to a corresponding second location (e.g., Room number 5 of a Patient Treatment Unit). It should be understood that a particular field (e.g., "SC 3^-ICU^PTU05^PTU05^UCLJ^^^^^^") of the transfer message 312 is indicated as corresponding to the assigned location ID 308 for ease of illustration, in some implementations one or more portions of the field, multiple fields of the transfer message 312, one or more portions of multiple fields of the transfer message 312, or a combination thereof, correspond to the assigned location ID 308.

In a particular aspect, the transfer message 312 corresponds to the first message 112. The healthcare listener 120 generates the second message 114 based on the transfer message 312. For example, the second message 114 includes the message type 202, the patient ID 206, the prior location ID 304, and the assigned location ID 308. The prior location ID 304 or the assigned location ID 308 may correspond to the location ID 204.

As described with reference to FIG. 2, the mobile device manager 234, based on the second message 114, determines that the patient 103 is no longer assigned to a first location corresponding to the prior location ID 304 (e.g., the location ID 204) and is assigned to a second location corresponding to the assigned location ID 308. The mobile device manager 234 may identify a first mobile device that was previously assigned to the patient 103. For example, the mobile device manager 234 determines that the first device was previously assigned to the patient 103 in response to determining that data in the memory 232 indicates that the patient ID 206 is associated with a device ID of the first mobile device. The mobile device manager 234 identifies, based on the location-to-device mapping data 210, a second mobile device assigned to the second location, as described with reference to FIG. 2.

In a particular aspect, the first mobile device is the same as the second mobile device. For example, the first mobile device is reassigned from the first location to the second location concurrently with the transfer of the patient 103 from the first location to the second location. The mobile device manager 234, in response to determining that the first device is the same as the second device, refrains from sending the reset command 135, the data 133, or both, to the device (e.g., the first device and the second device).

In a particular aspect, the first mobile device is distinct from the second mobile device. In this aspect, the mobile device manager 234, in response to determining that the patient 103 is no longer assigned to the first location, sends the reset command 135 to the first mobile device (e.g., the mobile device 150), removes an association between the patient 103 and the first mobile device from the memory 232, or both, as described with reference to FIG. 2. The mobile device manager 234, in response to determining that the patient 103 is assigned to the second location, may send the reset command 135 to the second mobile device (e.g., the mobile device 150), send the data 133 to the second mobile device, add an association between the patient 103 and the second mobile device in the memory 232, or a combination thereof. The transfer message 312 thus enables the mobile device manager 234 to automatically delete user information from the first mobile device, set up the second mobile device, or both.

Referring to FIG. 4, a discharge message is shown and generally designated 412. The discharge message 412 may be generated by the healthcare management system 110, the healthcare listener 120, the system 100 of FIG. 1, or a combination thereof. The discharge message 412 may correspond to the first message 112, the second message 114 of FIG. 1, or both. The discharge message 412 may comply with an ADT message specification. In a particular aspect, the discharge message 412 complies with a HL7 format. For example, the discharge message 412 complies with a HL7 version 1 format, a HL7 version 2 format, a HL7 version 3 format, a HL7 FHIR format, another HL7 format, or a combination thereof.

The discharge message 412 indicates the message type 202 (e.g., "A03"). A value (e.g., "A03") of the message type 202 indicates that the discharge message 412 corresponds to a discharge message. The discharge message 412 indicates the patient ID 206 (e.g., "30001055"). A value (e.g., "30001055") of the patient ID 206 indicates that the corresponding patient 103 is discharged. The discharge message 412 indicates the location ID 204 (e.g., "HC 2-SICU^ICU10^ICU10^^UCHC^10^^^^^"). A value (e.g., "HC 2-SICU^ICU10^ICU10^^UCHC^10^^^^^") of the location ID 204 indicates that the patient 103 is discharged from a corresponding location (e.g., Room number 10A of a Care Unit). It should be understood that a particular field (e.g., "HC 2-SICU^ICU10^ICU10^^UCHC^10^^^^^") of the discharge message 412 is indicated as corresponding to the location ID 204 for ease of illustration, in some implementations one or more portions of the field, multiple fields of the discharge message 412, one or more portions of multiple fields of the discharge message 412, or a combination thereof, correspond to the location ID 204.

In a particular aspect, the discharge message 412 corresponds to the first message 112. The healthcare listener 120 generates the second message 114 based on the discharge message 412. For example, the second message 114 includes the message type 202, the patient ID 206, and the location ID 204.

As described with reference to FIG. 2, the mobile device manager 234, based on the second message 114, determines that the patient 103 is no longer assigned to the particular location corresponding to the location ID 204. The mobile device manager 234 may identify the mobile device 150 in response to determining that data in the memory 232 indicates that the patient ID 206 is associated with the device ID 214. Alternatively, the mobile device manager 234 may identify the mobile device 150 based on the location ID 204 and the location-to-device mapping data 210, as described with reference to FIG. 2.

The mobile device manager 234 may, in response to determining that the patient 103 is no longer assigned to the particular location, send the reset command 135 to the mobile device 150, remove an association between the patient 103 and the mobile device 150 from the memory 232, or both, as described with reference to FIG. 2. The discharge message 412 thus enables the mobile device manager 234 to automatically delete user information (e.g., the data 133 of FIG. 1) from the mobile device 150.

Figure 5:
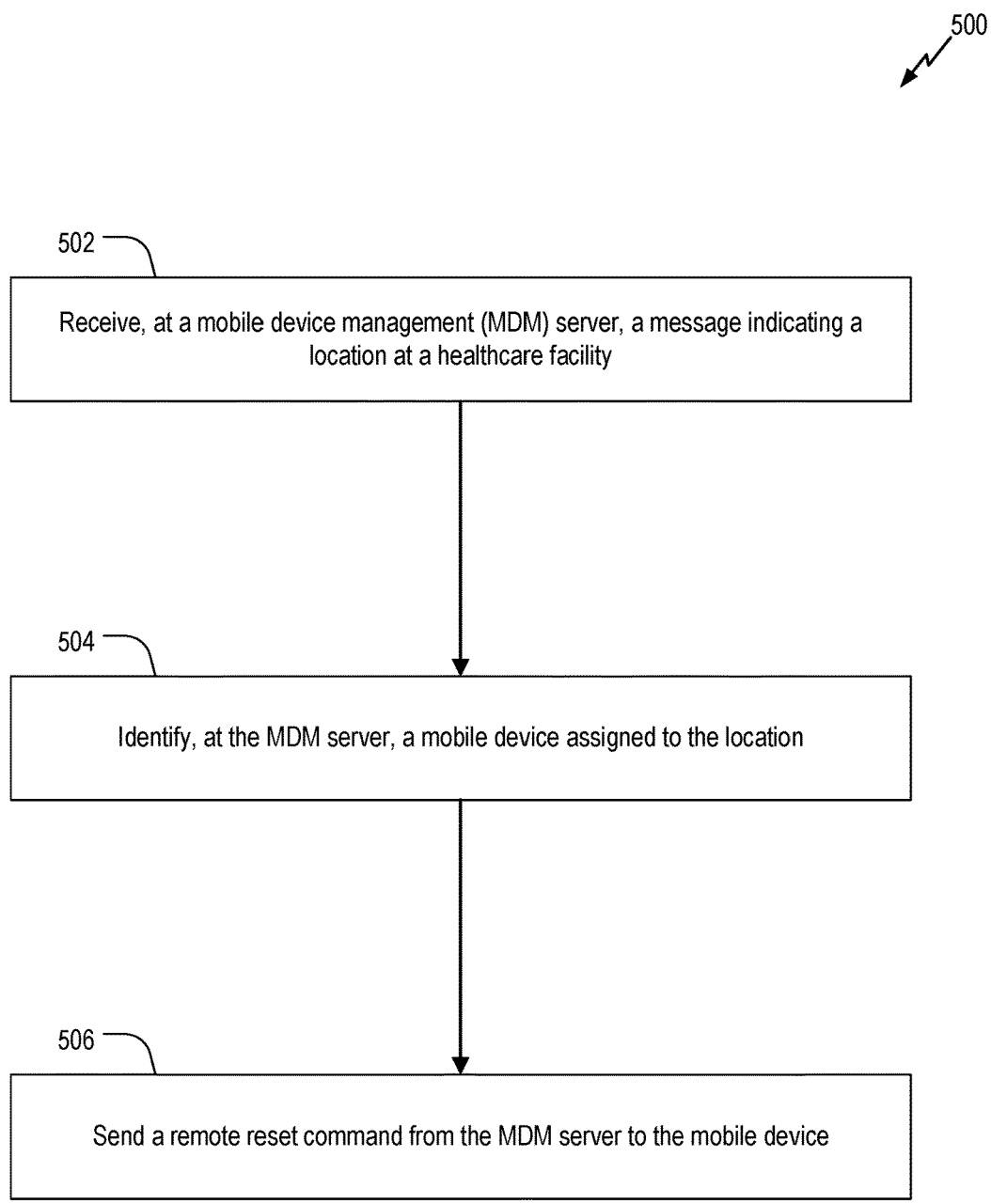
FIG. 5 is a flow chart of a method of mobile device management.

Referring to FIG. 5, a method of mobile device management is shown and generally designated 500. The method 500 may be performed by the MDM server 130, the system 100 of FIG. 1, the mobile device manager 234, the system 200 of FIG. 2, or a combination thereof.

The method 500 includes receiving, at a mobile device management (MDM) server, a message indicating a location at a healthcare facility, at 502. For example, the MDM server of FIG. 1 receives the second message 114 including the location ID 204 of FIG. 2. The location ID 204 may indicate a location at a healthcare facility, as described with reference to FIG. 2.

The method 500 also includes identifying, at the MDM server, a mobile device assigned to the location, at 504. For example, the MDM server 130 identifies the mobile device 150 assigned to the location corresponding to the location ID 204, as further described with reference to FIG. 2.

The method 500 further includes sending a remote reset command from the MDM server to the mobile device, at 506. For example, the mobile device manager 234 sends the reset command 135 (e.g., a remote reset command) from the MDM server 130 to the mobile device 150, as described with reference to FIG. 2.

The method 500 thus enables the MDM server 130 to automatically send the reset command 135 to the mobile device 150 in response to receiving the second message 114. The mobile device 150 may, in response to receiving the reset command 135, delete personally identifiable user information stored at the mobile device 150. The MDM server 130 thus reduces (e.g., eliminates) the likelihood of the patient 103 accessing sensitive information associated with a previous user of the mobile device 150.

Figure 6:
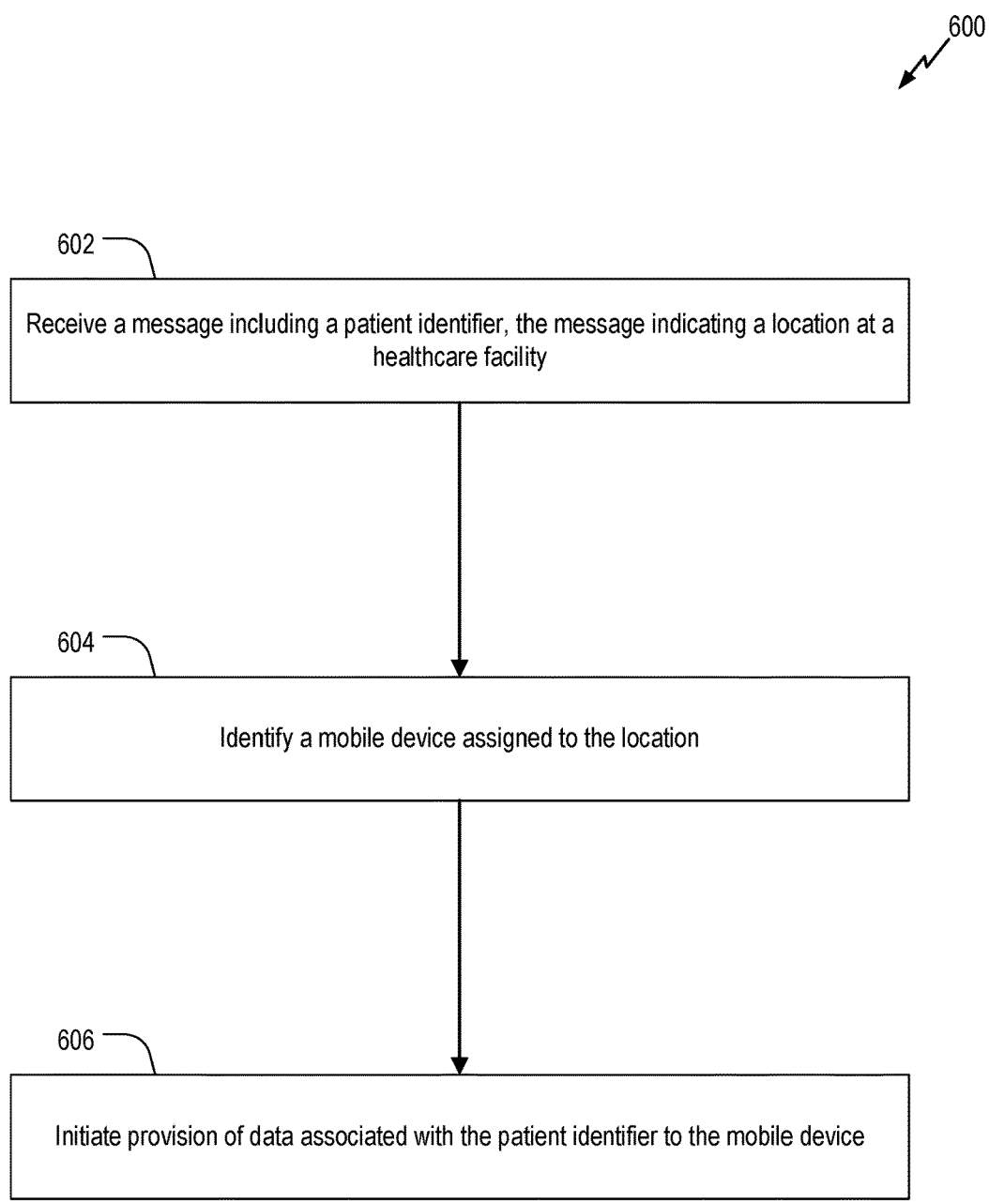
FIG. 6 is a flow chart of a method of mobile device management.

Referring to FIG. 6, a method of mobile device management is shown and generally designated 600. The method 600 may be performed by the healthcare listener 120, the MDM server 130, the system 100 of FIG. 1, the mobile device manager 234, the system 200 of FIG. 2, or a combination thereof.

The method 600 includes receiving a message including a patient identifier, at 602. For example, the healthcare listener 120 receives the first message 112 including the patient ID 206. The first message 112 includes the location ID 204 indicating a location at a healthcare facility, as further described with reference to FIG. 2. As another example, the mobile device manager 234 receives the second message 114 including the patient ID 206. The second message 114 includes the location ID 204 indicating a location at a healthcare facility, as further described with reference to FIG. 2.

The method 600 also includes identifying a mobile device assigned to the location, at 604. For example, the mobile device manager 234 identifies the mobile device 150 assigned to the location corresponding to the location ID 204, as described with reference to FIG. 2.

The method 600 further includes initiating provision of data associated with the patient identifier to the mobile device, at 606. For example, the healthcare listener 120 sends the second message 114 to the MDM server 130 to initiate provision of the data 133 associated with the patient ID 206 from the MDM server 130 to the mobile device 150. As another example, the mobile device manager 234 initiates provision of the data 133 to the mobile device 150 by sending the notification request 124 to the push notification service 140, sending the data 133 to the mobile device 150, or both.

The method 600 thus enables the MDM server 130 to automatically provide the data 133 associated with the patient 103 to the mobile device 150 in response to receiving the second message 114. The MDM server 130 thus automatically sets up (e.g., configures) the mobile device 150 for use by patient 103.

Figure 7:
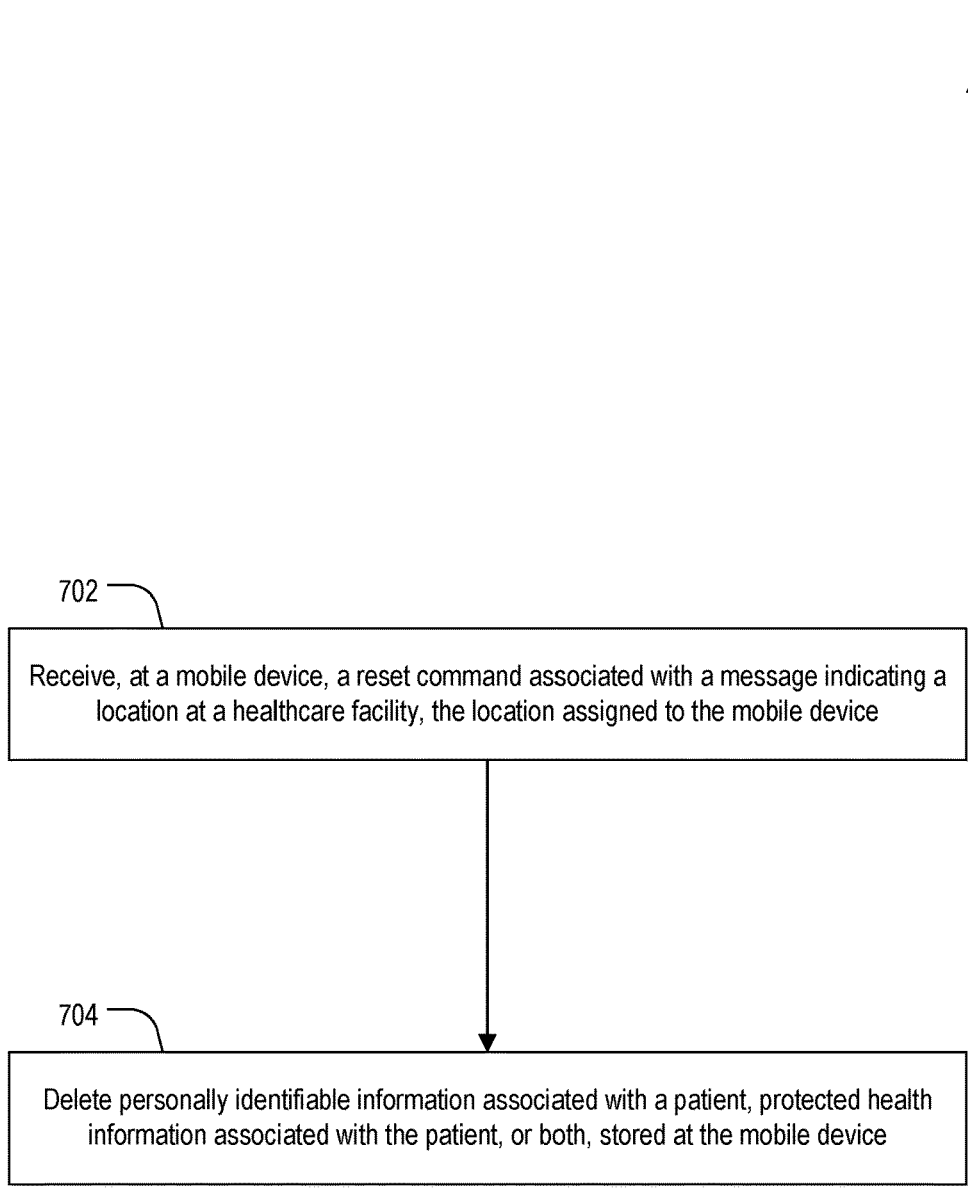
FIG. 7 is a flow chart of a method of mobile device management.

Referring to FIG. 7, a method of mobile device management is shown and generally designated 700. The method 700 may be performed by the mobile device 150, the system 100 of FIG. 1, the system 200 of FIG. 2, or a combination thereof.

The method 700 includes receiving, at a mobile device, a reset command associated with a message indicating a location at a healthcare facility, the location assigned to the mobile device, at 702. For example, the mobile device 150 of FIG. 1 receives the reset command 135. The reset command 135 is associated with the first message 112, the second message 114, or both. The first message 112, the second message 114, or both, include the location ID 204 indicating a location at a healthcare facility, as described with reference to FIG. 2.

The method 700 also includes deleting personally identifiable information associated with a patient, protected health information associated with the patient, or both, stored at the mobile device, at 704. For example, the mobile device 150 of FIG. 1 deletes the data 133 stored at the mobile device 150. The data 133 may include the patient record 222, the medical information 224, the application data 226, the configuration setting 228, or a combination thereof. The patient record 222, the medical information 224, the application data 226, the configuration setting 228, or a combination thereof, corresponds to personally identifiable information associated with the patient 103, protected health information associated with the patient 103, or both.

The method 700 thus enables the mobile device 150 to delete personally identifiable information associated with the patient 103, protected health information associated with the patient 103, or both. The mobile device 150 thus reduces (e.g., eliminates) the likelihood of sensitive information of the patient 103 being accessed by a subsequent user of the mobile device 150.

Although one or more of FIGS. 1-7 may illustrate systems, devices, and/or methods according to the teachings of the disclosure, the disclosure is not limited to these illustrated systems, devices, and/or methods. Aspects of the disclosure may be suitably employed in any device that includes integrated circuitry including memory, a processor, and on-chip circuitry.

One or more functions or components of any of FIGS. 1-7 as illustrated or described herein may be combined with one or more other portions of another of FIGS. 1-7. Accordingly, no single aspect described herein should be construed as limiting and aspects of the disclosure may be suitably combined without departing form the teachings of the disclosure.

Those of skill would further appreciate that the various illustrative logical blocks, configurations, modules, circuits, and algorithm steps described in connection with the aspects disclosed herein may be implemented as electronic hardware, computer software executed by a processor, or combinations of both. Various illustrative components, blocks, configurations, modules, circuits, and steps have been described above generally in terms of their functionality. Whether such functionality is implemented as hardware or processor executable instructions depends upon the particular application and design constraints imposed on the overall system. Skilled artisans may implement the described functionality in varying ways for each particular application, but such implementation decisions should not be interpreted as causing a departure from the scope of the present disclosure.

The steps of a method or algorithm described in connection with the aspects disclosed herein may be embodied directly in hardware, in a software module executed by a processor, or in a combination of the two. A software module may reside in random access memory (RAM), flash memory, read-only memory (ROM), programmable read-only memory (PROM), erasable programmable read-only memory (EPROM), electrically erasable programmable read-only memory (EEPROM), registers, hard disk, a removable disk, a compact disc read-only memory (CD-ROM), or any other form of non-transient storage medium known in the art. An exemplary storage medium (e.g., a computer-readable storage device) is coupled to the processor such that the processor can read information from, and write information to, the storage medium. In the alternative, the storage medium may be integral to the processor. The processor and the storage medium may reside in an application-specific integrated circuit (ASIC). The ASIC may reside in a computing device or a user terminal. In the alternative, the processor and the storage medium may reside as discrete components in a computing device or user terminal. A storage device is not a signal.

The previous description of the disclosed aspects is provided to enable a person skilled in the art to make or use the disclosed aspects. Various modifications to these aspects will be readily apparent to those skilled in the art, and the principles defined herein may be applied to other aspects without departing from the scope of the disclosure. Thus, the present disclosure is not intended to be limited to the aspects shown herein but is to be accorded the widest scope possible consistent with the principles and novel features as defined by the following claims.

What is claimed is:

1. A method comprising:
    storing, at a mobile device management (MDM) server, location-to-device mapping data indicating mobile devices assigned to locations at a healthcare facility, wherein the location-to-device mapping data indicates that a first mobile device is assigned to a first location at the healthcare facility and that a second mobile device is assigned to a second location at the healthcare facility, and wherein the first location is distinct from the second location;
    receiving, at the MDM server, a message indicating receipt of user input that indicates a patient identifier and a particular location associated with a patient;
    in response to determining, based on the location-to-device mapping data, that the particular location corresponds to the first location:
        associating the patient with the first mobile device;
        selecting a selected entertainment application based on a patient record associated with the patient identifier, wherein the selected entertainment application is targeted to the patient based on the patient record;
        sending configuration setting data to the mobile device, the configuration setting data triggering the first mobile device to provide a username and password to a web-based healthcare application to:
            enable the patient to access the web-based healthcare application without entering the username and password; and
            prompt the patient to verify patient information in the web-based healthcare application; and
        sending application data to the mobile device based on selecting the selected entertainment application, the application data triggering the first mobile device to retrieve the selected entertainment application;
    sending healthcare information associated with the patient to the first mobile device, the healthcare information stored in a database accessible to the MDM server; and
    in response to determining that the patient is no longer associated with the first mobile device, sending a remote command from the MDM server to the first mobile device to erase the healthcare information associated with the patient stored in a memory device of the first mobile device.

2. The method of claim 1, wherein the healthcare information includes personally identifiable information associated with the patient; and wherein the remote command indicates that the personally identifiable information associated with the patient, the healthcare information associated with the patient, or both, are to be deleted from the first mobile device.

3. The method of claim 1, wherein the remote command includes a factory reset command.

4. The method of claim 1, further comprising:
    sending a notification request from the MDM server to a push notification service to initiate transmission of a push notification from the push notification service to the first mobile device; and
    receiving, at the MDM server, a second message from the first mobile device responsive to the push notification.

5. The method of claim 1, further comprising:
    selecting a manifest file based on the patient record, wherein the manifest file indicates at least one application, and wherein the healthcare information indicates the manifest file and is sent to the first mobile device to enable the first mobile device to access the at least one application.

6. The method of claim 1, wherein the message includes an admit message indicating that the patient is associated with the particular location, and wherein the remote command indicates that the healthcare information associated with the patient is to be deleted from the first mobile device.

7. The method of claim 1, further comprising selecting, based on the patient identifier, at least one of a patient record, a configuration setting, medical information, or application data, wherein the healthcare information sent to the first mobile device includes the at least one of the patient record, the configuration setting, the medical information, or the application data.

8. The method of claim 1, further comprising disassociating the patient with the first mobile device in response to receiving a second message, wherein the second message indicates that the particular location associated with the patient has changed, the patient has been discharged from the healthcare facility, the patient has been transferred to another location, or another patient has been associated with the first location.

9. The method of claim 1, wherein the message complies with a health level seven (HL7) format.

10. The method of claim 1, wherein the web-based healthcare application notifies hospital personnel in response to an indication by the patient that the patient information in the web-based healthcare application is inaccurate.

11. The method of claim 10, wherein the patient information includes an education level of the patient, a diagnosis of the patient, an allergy information associated with the patient.

12. The method of claim 11, wherein the web-based healthcare enables the patient to make healthcare decisions based on the education level, the diagnosis, and the allergy information.

13. A computer-readable storage device storing instructions that, when executed by a processor, cause the processor to perform operations comprising:
    storing location-to-device mapping data indicating mobile devices assigned to locations at a healthcare facility, wherein the location-to-device mapping data indicates that a first mobile device is assigned to a first location at the healthcare facility and that a second mobile device is assigned to a second location at the healthcare facility, and wherein the first location is distinct from the second location;
    receiving a message indicating receipt of user input indicating a patient identifier and a particular location associated with a patient;
    in response to determining, based on the location-to-device mapping data, that the particular location corresponds to the first location:

associating the patient with the first mobile device;

selecting a selected entertainment application based on a patient record associated with the patient identifier, wherein the selected entertainment application is targeted to the patient based on the patient record;

sending configuration setting data to the mobile device, the configuration setting data triggering the first mobile device to provide a username and password to a web-based healthcare application to:
- enable the patient to access the web-based healthcare application without entering the username and password; and
- prompt the patient to verify patient information in the web-based healthcare application; and sending application data to the mobile device based on selecting the selected entertainment application, the application data triggering the first mobile device to retrieve the selected entertainment application;

initiating provision of healthcare information associated with the patient to the first mobile device, the healthcare information stored in a database; and in response to determining that the patient is no longer associated with the first mobile device, sending a remote command to the first mobile device to initiate deletion of the healthcare information associated with the patient stored in a memory device of the first mobile device.

14. The computer-readable storage device of claim 13, wherein the healthcare information associated with the patient includes a patient record, medical information, application data, a configuration setting, or a combination thereof.

15. The computer-readable storage device of claim 13, wherein the message indicates that the patient is admitted to the healthcare facility.

16. The computer-readable storage device of claim 13, further comprising disassociating the patient with the first mobile device in response to receiving a second message, wherein the second message indicates that the particular location associated with the patient has changed, the patient has been discharged from the healthcare facility, the patient has been transferred to another location, or another patient has been associated with the first location.

17. The computer-readable storage device of claim 16, further comprising subsequent to sending the remote command to the first mobile device, sending healthcare information associated with the second patient to the first mobile device, wherein the second patient has been associated with the first mobile device.

18. A computer system comprising:
a healthcare listener device configured to:
- receive a first message indicating receipt of user input indicating a patient identifier and a particular location associated with a patient at a healthcare facility; and
- send a second message to a mobile device management (MDM) server indicating the patient identifier and the particular location; and the MDM server configured to:
- store location-to-device mapping data indicating mobile devices assigned to locations at the healthcare facility, the locations including a first location, wherein the location-to-device mapping data indicates that a first mobile device is assigned to the first location and that a second mobile device is assigned to a second location at the healthcare facility, and wherein the first location is distinct from the second location; and
- in response to determining, based on the location-to-device mapping data, that the particular location corresponds to the first location:
  - associate the patient with the first mobile device;
  - select a selected entertainment application based on a patient record associated with the patient identifier, wherein the selected entertainment application is targeted to the patient based on the patient record;
  - send configuration setting data to the mobile device, the configuration setting data triggering the first mobile device to provide a username and password to a web-based healthcare application to:
    - enable the patient to access the web-based healthcare application without entering the username and password; and
    - prompt the patient to verify patient information in the web-based healthcare application; and
  - send application data to the mobile device based on selecting the selected entertainment application, the application data triggering the first mobile device to retrieve the selected entertainment application;
- send healthcare information associated with the patient to the first mobile device, the healthcare information stored in a database accessible to the MDM server; and
- in response to determining that the patient is no longer associated with the first mobile device, send a remote command to the first mobile device to cause the first mobile device to erase the healthcare information associated with the patient stored in a memory device of the first mobile device.

19. The computer system of claim 18, wherein the MDM server is further configured to:
- send a notification request to a push notification service to initiate transmission of a push notification to the first mobile device; and
- receive a message from the first mobile device responsive to the push notification.

20. The computer system of claim 18, wherein the MDM server is further configured to:
- send a notification request to a push notification service to initiate transmission of a push notification to the first mobile device; and
- generate an alert in response to determining that a message has not been received from the first mobile device within a particular duration of sending the notification request to the push notification service.

* * * * *